(12) United States Patent
Zhao et al.

(10) Patent No.: US 12,396,705 B2
(45) Date of Patent: Aug. 26, 2025

(54) SCANNING ASSEMBLY AND ULTRASOUND IMAGING DEVICE

(71) Applicant: GE Precision Healthcare LLC, Waukesha, WI (US)

(72) Inventors: Hongyu Zhao, Wuxi (CN); Bo Dan, Wuxi (CN); Qiang Yao, Wuxi (CN); Chunyan Qi, Wuxi (CN); Kuo Wang, Wuxi (CN); Xin Wang, Wuxi (CN); Lu Jin, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 3 days.

(21) Appl. No.: 18/590,739

(22) Filed: Feb. 28, 2024

(65) Prior Publication Data

US 2024/0285254 A1   Aug. 29, 2024

(30) Foreign Application Priority Data

Feb. 28, 2023 (CN) .......................... 202310187979.7

(51) Int. Cl.
*A61B 8/08* (2006.01)
*A61B 8/00* (2006.01)

(52) U.S. Cl.
CPC .......... *A61B 8/4461* (2013.01); *A61B 8/0825* (2013.01); *A61B 8/403* (2013.01); *A61B 8/4281* (2013.01)

(58) Field of Classification Search
CPC ..... A61B 8/4461; A61B 8/403; A61B 8/4281; A61B 8/0825
See application file for complete search history.

(56) References Cited

U.S. PATENT DOCUMENTS

| | | | |
|---|---|---|---|
| 6,485,420 B1 | 11/2002 | Bullis | |
| 8,298,146 B2 | 10/2012 | Amara | |
| 9,420,991 B2 | 8/2016 | Wang | |
| 9,655,590 B2 | 5/2017 | Yu | |
| 11,020,086 B2 | 6/2021 | Wang | |
| 11,432,799 B2 * | 9/2022 | Tian ...................... | A61B 8/429 |
| 2010/0177866 A1 | 7/2010 | Shibuya | |
| 2012/0022376 A1 | 1/2012 | Amara | |
| 2013/0116570 A1 | 5/2013 | Carson | |
| 2017/0112467 A1 * | 4/2017 | Lenox ................... | A61B 8/403 |
| 2018/0168544 A1 * | 6/2018 | Davidsen ............. | A61B 8/4254 |

(Continued)

FOREIGN PATENT DOCUMENTS

EP         2570083 A1 *  3/2013  ........... A61B 6/0421
WO      2003103500 A1    12/2003

*Primary Examiner* — Colin T. Sakamoto

(57) ABSTRACT

A scanning assembly, including: a housing, wherein a lower portion of the housing comprises an opening, and the opening can be closed by tissue to be scanned; a pressure difference generating device, disposed on the housing and used to generate an air pressure difference between the interior and the exterior of the housing, the air pressure difference providing a first pressure for the tissue to be scanned, the weight of the scanning assembly providing a second pressure for the tissue to be scanned, the tissue to be scanned being compressed under the action of a compressive force, and the compressive force comprising the first pressure and the second pressure; and an ultrasonic transducer, disposed in the housing and used to perform ultrasound scanning on the compressed tissue to be scanned.

17 Claims, 5 Drawing Sheets

(56) References Cited

U.S. PATENT DOCUMENTS

| | | | |
|---|---|---|---|
| 2019/0090828 A1* | 3/2019 | Dederichs | A61B 8/4416 |
| 2019/0209129 A1* | 7/2019 | Choi | A61B 8/0825 |
| 2021/0022705 A1* | 1/2021 | Suzuki | A61B 8/15 |
| 2022/0192632 A1* | 6/2022 | Bambot | A61B 8/4416 |

* cited by examiner

-- Prior art --

SCANNING ASSEMBLY AND ULTRASOUND IMAGING DEVICE

CROSS-REFERENCE TO RELATED APPLICATION

The present application claims priority to Chinese Patent Application No. 202310187979.7, filed on Feb. 28, 2023. The entire contents of the above-listed application are incorporated by reference herein in their entirety.

TECHNICAL FIELD

The present application relates to the field of medical imaging, and relates in particular to a scanning assembly and an ultrasound imaging device.

BACKGROUND

Ultrasound imaging is a non-destructive and real-time imaging means, which can be used for scanning a variety of human organs and tissues. One of the examples is an automatic breast ultrasound imaging system which can perform ultrasound imaging on the breast of a person receiving a scan. In some examples, the automatic breast ultrasound imaging system includes a scanning assembly capable of scanning breasts. In order to perform high-quality imaging on breasts, it is generally necessary to apply an appropriate downward compressive force to the breasts. In order to ensure the safety of a person receiving a scan, it is further necessary to ensure that the compressive force is not set to be overly strong. Existing solutions include providing a balancing mechanism that includes a counterweight, and connecting the counterweight to a scanning assembly by means of an arm. The counterweight can balance the gravity of the scanning assembly to adjust, under the action of a driving mechanism, the downward pressure of the scanning assembly.

The above-described method for adjusting the compressive force solves, to some extent, the problem of how to reasonably adjust the compressive force on breasts, but still has notable defects. In one aspect, configurations of the counterweight and the arm obviously affect the range of movement of the scanning assembly, and during use, a scanning operator has to reasonably position the ultrasound imaging device and a person receiving a scan. In another aspect, providing structures such as the counterweight and the arm increases the complexity of the imaging device, thereby increasing the complexity of operations performed by a scanning operator.

SUMMARY

The aforementioned defects, deficiencies, and problems are solved herein, and these problems and solutions will be understood through reading and understanding the following description.

Provided in some embodiments of the present application is a scanning assembly, comprising: a housing, wherein a lower portion of the housing comprises an opening, and the opening can be closed by tissue to be scanned; a pressure difference generating device, disposed on the housing and used to generate an air pressure difference between the interior and the exterior of the housing, the air pressure difference providing a first pressure for the tissue to be scanned, the weight of the scanning assembly providing a second pressure for the tissue to be scanned, the tissue to be scanned being compressed under the action of a compressive force, and the compressive force comprising the first pressure and the second pressure; and an ultrasonic transducer, disposed in the housing and used to perform ultrasound scanning on the compressed tissue to be scanned. The present application also provides an ultrasound imaging device comprising the above-described scanning assembly.

Further provided in some other embodiments of the present application is an ultrasound imaging device, comprising the scanning assembly as described above.

It should be understood that the brief description above is provided to introduce, in a simplified form, concepts that will be further described in the detailed description. The brief description above is not meant to identify key or essential features of the claimed subject matter. The scope is defined uniquely by the claims that follow the detailed description. Furthermore, the claimed subject matter is not limited to implementations that solve any deficiencies raised above or in any section of the present disclosure.

BRIEF DESCRIPTION OF THE DRAWINGS

The present application will be better understood by reading the following description of non-limiting embodiments with reference to the accompanying drawings, wherein.

DETAILED DESCRIPTION

Specific embodiments of the present application are described below. It should be noted that in the specific description of said embodiments, for the sake of brevity and conciseness, the present description cannot describe all of the features of the actual embodiments in detail. It should be understood that in the actual implementation process of any embodiment, just as in the process of any one engineering project or design project, a variety of specific decisions are often made to achieve specific goals of the developer and to meet system-related or business-related constraints, which may also vary from one embodiment to another. Furthermore, it should also be understood that although efforts made in such development processes may be complex and extended, for a person of ordinary skill in the art related to the disclosure of the present application, some design, manufacture or production changes made on the basis of the technical disclosure of the present disclosure are only conventional technical means, and should not be construed that the content of the present disclosure is insufficient.

Unless otherwise defined, the technical or scientific terms used in the claims and the description should be as they are usually understood by those possessing ordinary skill in the technical field to which they belong. Terms such as "first", "second" and similar terms used in the present description and claims do not denote any order, quantity, or importance, but are only intended to distinguish different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections.

Although some embodiments of the present application are presented in a particular context of human breast ultrasound, it should be understood that the present application is applicable to performing an ultrasound scan on any externally accessible human or animal body part (for example, the abdomen, legs, feet, arms, or neck).

Figure 1:
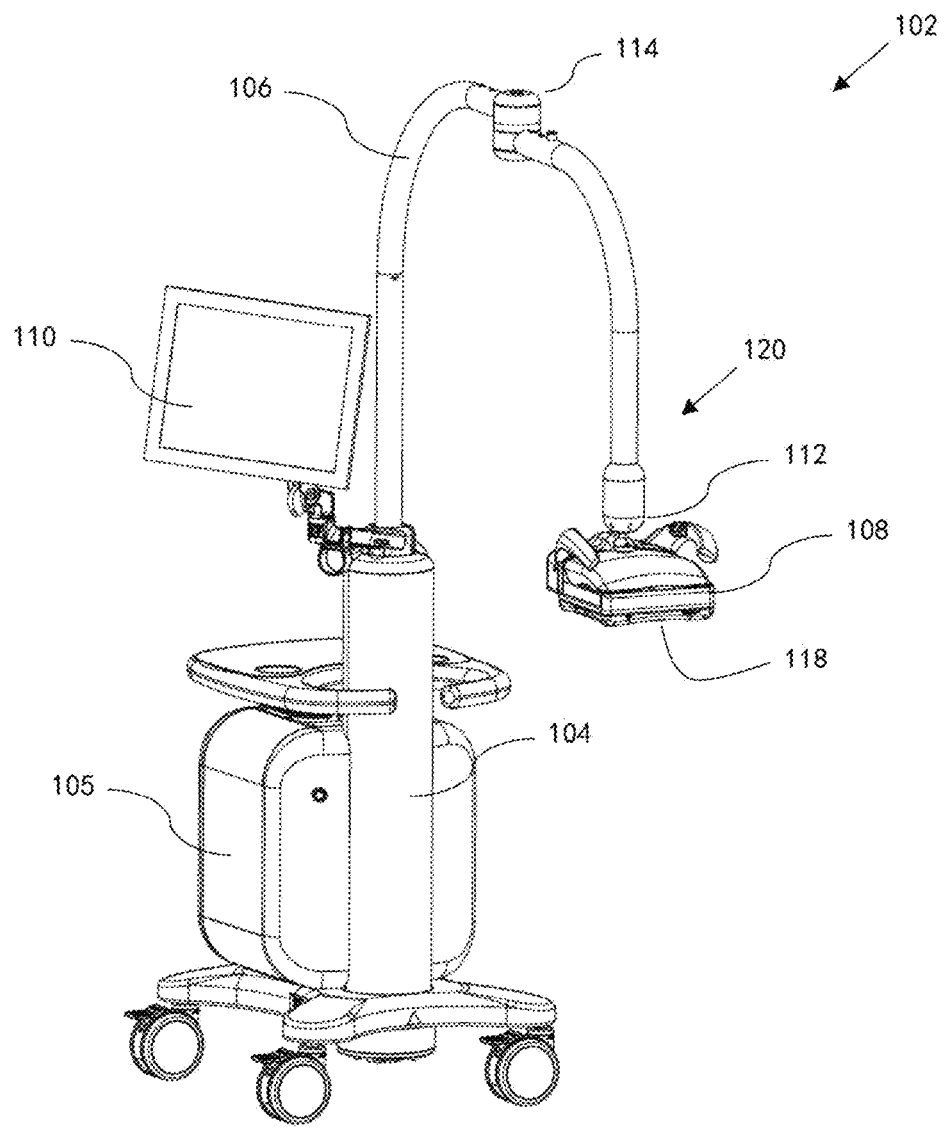
FIG. 1 shows a perspective view of an ultrasound imaging device in the prior art.

FIG. 1 shows a perspective view of an ultrasound imaging device 102 in the prior art. The body of the ultrasound imaging device 102 may include a main machine, a display 110, an adjustable arm 106, and a scanning assembly 108. The adjustable arm 106 and an internal balancing mechanism (e.g., a counterweight and a related connecting member) thereof can be used to balance the weight of the scanning assembly 108 and adjust, during ultrasound scanning, a compressive force applied by the scanning assembly 108 onto a person receiving a scan. The ultrasound imaging device 102 is exemplarily described below.

The ultrasound imaging device 102 may include a body frame 104, an ultrasonic processor housing 105 including an ultrasonic processor, a movable and adjustable support arm (for example, an adjustable arm) 106 including a hinge joint 114, a scanning assembly 108 connected to a first end 120 of the adjustable arm 106 by means of a ball-and-socket connector (for example, a ball joint) 112, and a display 110 connected to the body frame 104. The display 110 is connected to the body frame 104 at a joining point where the adjustable arm 106 enters the body frame 104. Since the display 110 is directly connected to the body frame 104 rather than the adjustable arm 106, the display 110 does not affect the weight of the adjustable arm 106 and a balancing mechanism of the adjustable arm 106.

The imaging device 102 shown in FIG. 1 allows a user to adjust the compressive force of the scanning assembly 108 on tissue to be scanned. An exemplary description is provided below. In one embodiment, the adjustable arm 106 is configured so that the scanning assembly 108 is substantially neutrally buoyant in a space, and in this case, the scanning assembly 108 can be operated to hover in any position within a certain height range. In another example, the adjustable arm 106 is configured so that the scanning assembly 108 has a light net downward weight (for example, 1-2 kg) for pressing down on the breasts, while allowing easy user operation. The scanning assembly 108 that is neutrally buoyant or has a light downward weight facilitates the movement of the scanning assembly 108 performed by the user to position the same on a surface of the tissue to be scanned. After the scanning assembly 108 is positioned, internal components of the ultrasound imaging device 102 may be adjusted to apply a desired downward weight for pressing down on the breast and improved image quality. In one example, the internal components may include a counterweight (not shown in the drawing). By controlling a balancing force of the counterweight on the scanning assembly 108, the user can control the compressive force of the scanning assembly 108 on the tissue to be scanned. In another example, the internal components may further include a motor and a transmission thereof (not shown in the drawing). The motor and the transmission thereof may be used to control the adjustment of the balancing force of the counterweight on the scanning assembly 108.

Further, the scanning assembly 108 may include a film 118 that is in a substantially tensioned state and that is at least partially attached, said film being used for pressing down on the breast. The film 118 has a bottom surface for making contact with the breast, and when the bottom surface makes contact with the breast, the transducer sweeps over a top surface of the film to scan the breast. In one example, the film is 118 a tensioned fabric sheet. In another example, the film 118 is a hard plastic sheet. The compressive force of the scanning assembly 108 can act on the tissue to be scanned by means of the film 118.

In order to improve the flexibility of movement of the scanning assembly 108, the ultrasound imaging device 102 is further configured to have an additional structure. In addition to the adjustable arm 106 and the counterweight that are exemplarily described above and that are adjustable in the vertical height direction, the adjustable arm 106 includes a hinge joint 114 to allow the scanning assembly 108 to move in the horizontal direction. The hinge joint 114 divides the adjustable arm 106 into a first arm portion and a second arm portion. The first arm portion is connected to the scanning assembly 108 and the second arm portion is connected to the body frame 104. The hinge joint 114 allows the second arm portion to rotate relative to the second arm portion and the body frame 104. For example, the hinge joint 114 allows the scanning assembly 108 to translate transversely and horizontally, but not vertically, relative to the second arm portion and the body frame 104. In such manner, the scanning assembly 108 can rotate toward the body frame 104 or away from the body frame 104. However, the hinge joint 114 is configured to allow the entire adjustable arm 106 (for example, the first arm portion and the second arm portion) to move vertically together as a whole (for example, translating upward and downward along with the body frame 104). By using the above means, the scanning assembly 108 can move vertically and/or horizontally within a certain range to move close to or away from a site to be scanned.

Optionally, the adjustable arm may include a potentiometer (not shown) to allow position and direction sensing performed by the pressing/scanning assembly 108, or may use other types of position and direction sensing (such as gyroscope, magnetic, optical, and radio frequency (RF)). A fully functional ultrasonic engine may be provided within the ultrasonic processor housing 105, and is configured to drive the ultrasonic transducer, and generate volumetric breast ultrasound data from a scan in conjunction with related position and orientation information. In some examples, volumetric scan data may be transmitted to another computer system by using any of a variety of data transmission methods known in the art so as to be further processed, or the volumetric scan data may be processed by the ultrasonic engine. A general-purpose computer/processor integrated with the ultrasonic engine may further be provided for general user interface and system control. The general-purpose computer may be a self-contained stand-alone unit, or may be remotely controlled, configured, and/or monitored by remote stations connected across networks.

In the ultrasound imaging device 102 illustrated above, the adjustable arm 106 is connected to the scanning assembly 108 to adjust the compressive force required by the scanning assembly 108 to perform ultrasound scanning, and can ensure that the compressive force is within a reasonable range so as to not put a person receiving a scan in danger. It is not difficult to see that the adjustable arm 106 includes a plurality of components, thereby increasing the complexity of operation performed by the user. Moreover, the scanning assembly 108 is connected to the adjustable arm 106, so that the range of movement of the scanning assembly 108 is limited by the range of movement of the adjustable arm 106. For example, in the horizontal direction, the scanning assembly 108 can move within a certain range around the hinge joint 114, and in the vertical direction, the scanning assembly 108 is restricted by the vertical travel of the adjustable arm 106.

In view of this, improvements are provided in embodiments of the present application in the hope of maintaining as much as possible the flexibility of scanning performed by a scanning assembly while ensuring that the compressive force of the scanning assembly on tissue to be scanned is configured to be within a reasonable and safe range.

Figure 2:
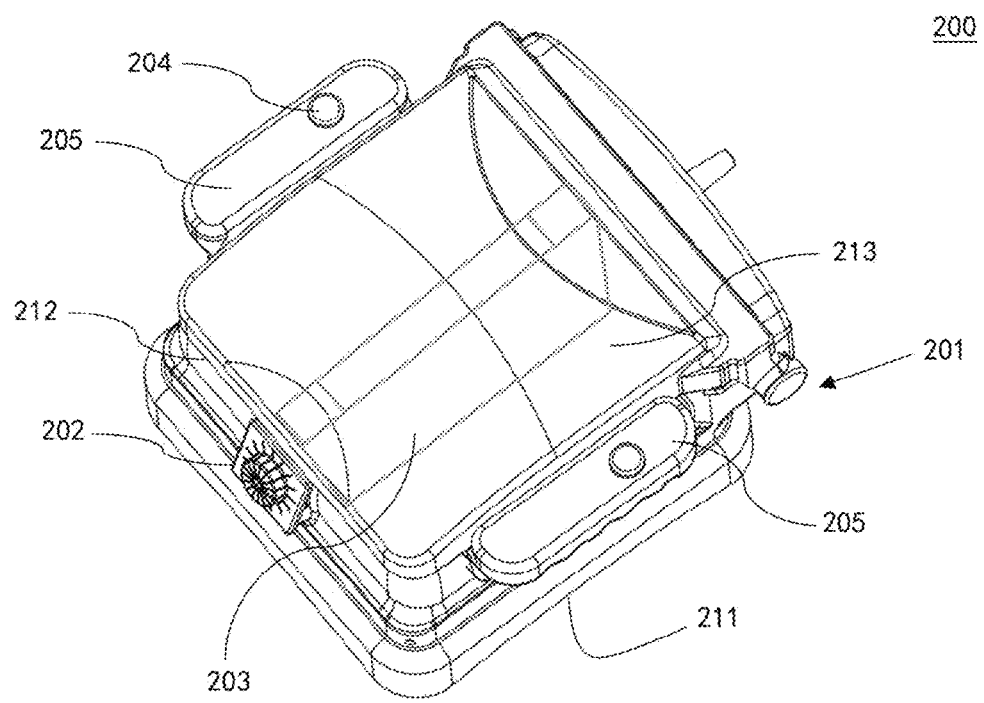
FIG. 2 shows a schematic diagram of a scanning assembly according to some embodiments of the present application.

Referring to FIG. 2, FIG. 2 shows a schematic diagram of a scanning assembly 200 according to some embodiments of the present application. The scanning assembly 200 is adapted to perform ultrasound scanning on a supine person receiving a scan. The scanning assembly 200 may include a housing 201, a pressure difference generating device 202, and an ultrasonic transducer 203.

A lower portion of the housing 201 may include an opening 211. The opening 211 can be closed by tissue to be scanned (not shown in FIG. 2).

The pressure difference generating device 202 is disposed on the housing 201, and is used to generate an air pressure difference between the interior and the exterior of the housing 201. The air pressure difference provides a first pressure for the tissue to be scanned, and the weight of the scanning assembly 200 provides a second pressure for the tissue to be scanned. The tissue to be scanned is compressed under the action of a compressive force, and the compressive force includes the first pressure and the second pressure.

The ultrasonic transducer 203 is disposed in the housing 201, and is used to perform ultrasound scanning on the compressed tissue to be scanned.

In such a configuration means, part of the compressive force on the tissue to be scanned is provided by the weight of the scanning assembly 200, and part is provided by the pressure difference generating device 202, so that no other additional assembly is further needed. The scanning assembly 200 can be moved with a high degree of freedom without being overly restricted by any additional structures (e.g., an adjustable arm or other assemblies). In addition, the pressure difference generating device 202 is disposed on the housing 201, i.e., as part of the entirety of the scanning assembly 200, and likewise does not need any additional connecting structures, and therefore the pressure difference generating device 202 likewise does not affect the flexibility of use of the scanning assembly 200.

In addition, the compressive force of the scanning assembly 200 of the present application on the tissue to be scanned at least includes two parts. One part is from the weight of the scanning assembly 200 (the second pressure), and the other part is from the pressure difference (the first pressure) generated by the pressure difference generating device 202 on the scanning assembly 200. The first pressure and the second pressure are of different types, so that the scanning assembly 200 of the present application has higher safety and operability. Since the pressure difference generating device 202 can be used to provide the first pressure as the compressive force, the scanning assembly 200 that uses the weight thereof to provide the second pressure can be configured to be light (e.g., less than 3 kilograms). In this way, when scanning is performed on the person receiving a scan, there is no danger even if the weight of the entire scanning assembly 200 acts on the person receiving a scan. Moreover, since the weight of the scanning assembly 200 acting as the second pressure can provide part of the compressive force, the first pressure provided by the pressure difference generating device 202 does not need to be overly high. In this way, the air pressure difference between the interior and the exterior of the scanning assembly 200 is not so large that the skin surface of the person receiving a scan will be injured due to a negative pressure. It should be noted that in some embodiments, the sum of the first pressure and the second pressure is the compressive force of the scanning assembly 200 on the tissue to be scanned. In some other embodiments, the compressive force may further include another force, e.g., an appropriate downward pressure applied by a scanning operator operating the scanning assembly 200. Examples are not exhaustively enumerated.

It can be understood that the material and shape of the housing 201 in the above embodiments may be arbitrary. In one embodiment, the housing 201 may include a transparent high-molecular polymer to facilitate the scanning operator to observe, through the housing 201, a scanned site and scanning condition of a probe. In another embodiment, the housing 201 may further include a metal material to improve the rigidity of the entire scanning assembly 200. The shape of the housing 201 may be an arbitrary shape, such as a circle, a rectangle, etc. Correspondingly, the shape of the opening 211 of the lower portion of the housing 201 may also be arbitrary, as long as the opening 211 and the tissue to be scanned can cooperate with each other to form a substantially closed space, so as to facilitate the pressure difference generating device 202 to generate the air pressure difference between the interior and the exterior of the scanning assembly 200. Moreover, the housing 201 may further include different components. For example, as shown in FIG. 2, the housing 201 may include a surrounding frame 212 and a cover 213 located above. The cover 213 may be made of a transparent material to facilitate the scanning operator to observe the scanning assembly 200. The frame 212 may have a certain thickness to facilitate integration therein of a cable or another structure. In one example, the cover 213 may be fixedly connected to the frame 212. In another example, the cover 213 may be detachably/movably connected to the frame 212. Such a configuration means facilitates the scanning operator to clean and sterilize the interior of the scanning assembly 200 when needed.

With continued reference to FIG. 2, the pressure difference generating device 202 may be disposed in any position on the housing 201. For example, the pressure difference generating device 202 may be disposed on the frame 212 of the housing 201. On the basis that the tissue to be scanned closes the opening 211 to cause a closed space to be formed between the scanning assembly 200 and the tissue to be scanned, the pressure difference generating device 202 can pump air from the closed space out of the space so as to generate an air pressure difference between the interior and the exterior of the closed space. The air pressure difference causes the scanning assembly 200 to press down on the tissue to be scanned. Since in the present application, part of the compressive force on the tissue to be scanned is provided by the weight of the scanning assembly 200, the pressure difference generating device 202 does not need to generate a pressure difference of very high power. Therefore, as shown in FIG. 2, the pressure difference generating device 202 can be configured to have smaller power and size, and be integrated on the housing 201 of the scanning assembly 200. The pressure difference generating device 202 is an independent device disposed on the housing 201, and does not need any external apparatuses (e.g., a vacuuming device, or the like).

Considering that compressive forces needed by different persons receiving a scan may be different and that even the same person receiving a scan may need different compressive forces depending on different compression conditions, improvements are provided in some embodiments of the present application. In some embodiments, the pressure difference generating device 202 is configured to be capable of adjusting the magnitude of the air pressure difference, to thereby adjust the first pressure. The above-described adjustment method may be implemented by changing the power of the pressure difference generating device 202. When the pressure difference generating device 202 operates at higher power, more air is drawn out from the closed space between the scanning assembly 200 and the tissue to be scanned, thereby resulting in a greater air pressure drop. At which time, the air pressure difference is increased. When the pressure difference generating device 202 operates at lower power, less air is drawn out from the closed space. At which time, the air pressure drop is smaller, and thus the air pressure difference is smaller.

In some embodiments, the pressure difference generating device 202 may include a fan. The rotational speed of the fan may be configured to be adjustable, thereby enabling the magnitude of the air pressure difference to be adjusted. As shown in FIG. 2, the pressure difference generating device 202 including the fan may be configured to communicate with the interior and the exterior of the housing 201 so as to remove air from an internal space of the scanning assembly to the outside to generate a pressure difference.

The fan acting as the pressure difference generating device 202 has advantages in a plurality of aspects. In one aspect, as compared with other negative pressure devices, such as a pump, pumping power of the fan is not overly high and thus does not pose a danger even if an error occurs during use of the scanning assembly 200. In addition, as described herein above, the scanning assembly 200 of the present application provides part of the compressive force by means of the weight thereof, and therefore the problem in which the compressive force provided by the fan is not sufficient does not occur. In another aspect, air channels inside and outside of the fan are connected, so that once a person receiving a scan feels uncomfortable, only a power-off operation is required to ensure that the pressure difference between the interior and the exterior rapidly returns to a balanced state, thereby rapidly removing the first pressure. The pressure difference generating device 202 of the present application can further ensure the safety of the person receiving a scan.

It can be understood that although FIG. 2 shows only one pressure difference generating device 202, a plurality of pressure difference generating devices 202 may be provided in other embodiments of the present application. For example, a plurality of pressure difference generating devices 202 may be uniformly disposed on the housing. In one aspect, a plurality of pressure difference generating devices 202 can further increase the first pressure. In another aspect, a plurality of pressure difference generating devices 202 being uniformly disposed can further ensure that the downward pressure between the scanning assembly 200 and the tissue to be scanned is balanced, thereby ensuring that a high-quality ultrasound scanning image can be acquired.

Taking into consideration the faster control of the pressure difference generating device 202, in some embodiments, the scanning assembly 200 may further include a control unit 204. The control unit 204 is configured to, when operated, control the pressure difference generating device 202 to adjust the magnitude of the first pressure to thereby adjust the magnitude of the compressive force. The control unit 204 is provided, so that the magnitude of the compressive force can be easily adjusted without any additional complex compressive force adjustment device, and high-quality imaging is facilitated.

In some embodiments, the control unit 204 may include a button. Correspondingly, a user may operate the control unit 204 by pressing or other means. In a non-limiting embodiment, the user can control, by pressing the control unit 204, the pressure difference generating device 202 to gradually adjust the increase of the first pressure, thereby increasing the compressive force.

It should be noted that FIG. 2 shows one control unit 204, but in some other embodiments of the present application, a plurality of buttons may be included, and different buttons may be configured to perform different functions. For example, one of the buttons is used to adjust the first pressure to increase the same, and another one of the buttons is used to adjust the first pressure to decrease the same, thereby making it easier for the user to adjust the pressure. In addition, in another embodiment, the control unit 204 may also be of another type other than a button. For example, the control unit 204 may be a key having a sliding function, and the user may control the first pressure by sliding the control unit 204. The foregoing will not be further enumerated.

In some embodiments, the pressure difference generating device 202 is further configured to, when the control unit 204 is not operated, adjust the magnitude of the first pressure to keep the compressive force stable. Such a configuration means decreases the operating difficulty of the user. For example, when the user operates the control unit 204 to control the compressive force to be at an ideal level, the user does not need to continuously maintain control of the control unit 204, and only needs to stop operating the control unit 204 (e.g., to stop pressing the button); at which time, the pressure difference generating device 202 continuously operates to automatically adjust the magnitude of the first pressure, thereby keeping the compressive force stable.

In some embodiments, the scanning assembly 200 may further include a handle 205. The handle 205 helps the user to hold the scanning assembly 200 and position the same on the surface of the body of the person receiving a scan to perform ultrasound scanning. As shown in FIG. 2, the handle 205 may be disposed on the housing 201, and the control unit 204 may be disposed on the handle 205. In such a configuration means, the user can, during ultrasound scanning, operate the control unit 204 while holding the handle 205 with two hands, thereby ensuring the continuity and stability of the scanning process. In one example, two oppositely arranged handles 205 may be included, and the user holding the same with two hands can more easily keep the scanning assembly 200 balanced.

It should be noted that, although internal electrical connection structures between components are not shown in FIG. 2, these connection means may be arbitrary ones in the prior art. For example, the components may be connected to each other by means of a cable or the like, and the cable may be disposed inside the housing 201. The foregoing will not be described any further.

Figure 3:
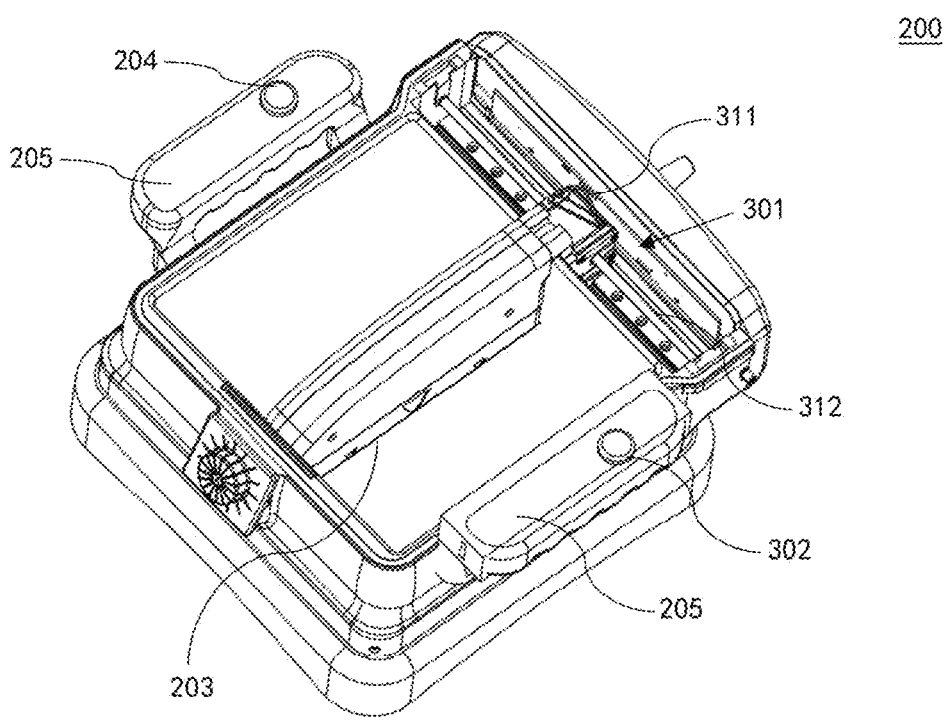
FIG. 3 shows a schematic diagram of a scanning assembly from which part of the top structure has been removed according to some embodiments of the present application.

After the scanning assembly 200 generates an appropriate compressive force on the tissue to be scanned, the ultrasonic transducer 203 in the scanning assembly 200 may be operated to perform ultrasound scanning on the tissue to be scanned. In some examples, the scanning assembly 200 is further provided with a driving device to drive the ultrasonic transducer 203, thereby performing automatic scanning. Referring to FIG. 3, FIG. 3 shows a schematic diagram of the scanning assembly 200 from which some top structures have been removed according to some embodiments of the present application.

As shown in FIG. 3, the scanning assembly 200 may include a driving device 301. The driving device 301 is connected to the ultrasonic transducer 203 to drive the ultrasonic transducer 203 to move. Such a configuration means enables the ultrasonic transducer 203 to automatically scan the tissue to be scanned. The user does not need to hold the ultrasonic transducer 203 with their hands and move during scanning, and only needs to pay attention to the positioning of the scanning assembly 200, thereby enhancing the degree of automation.

The driving device 301 may drive, in using a variety of means, the ultrasonic transducer 203 to move. In one embodiment, the driving device 301 includes a motor 311 and a lead screw 312. The lead screw 312 is horizontally disposed inside the housing 201, and is connected to the ultrasonic transducer 203. The motor 311 and the lead screw 312 cooperate with each other to drive the ultrasonic transducer 203 to move in the horizontal direction. As shown in FIG. 3, the motor 311 is connected to one end of the ultrasonic transducer 203, and is connected to the lead screw 312 by means of a thread. In the threaded connection means, an inner thread may be disposed on the motor 311, and the lead screw 312 passes through the inner thread. In this way, when the motor 311 drives the inner thread to rotate, the inner thread can move in the horizontal direction relative to the lead screw 312 and drive the ultrasonic transducer 203 to move horizontally.

It can be understood that the motor 311 and the lead screw 312 may cooperate in other means. For example, the motor 311 and the lead screw 312 are both fixed, and the lead screw 312 is driven to rotate to drive the ultrasonic transducer 203 to move, or the like. Moreover, in another embodiment, the driving device may also be configured to drive the ultrasonic transducer to rotate in the housing of the scanning assembly 200. Examples are not exhaustively enumerated.

In a suitable occasion, the driving device 301 may drive the ultrasonic transducer 203 to move, so as to perform ultrasound scanning on the tissue to be scanned. In one embodiment, the above-described occasion may be controlled by the user. For example, as shown in FIG. 3, the scanning assembly 200 may include a button 302. The button 302 may be used to control the operation of the driving device 301. When the button 302 is pressed by the user, the driving device 301 may continuously drive the movement of the ultrasonic transducer 203. When the button 302 is not pressed, the driving device 301 stops operating, and the ultrasonic transducer 203 no longer moves. By adjusting the operational state of the button 302, the user can flexibly control the movement of the ultrasonic transducer 203 according to actual scanning conditions. In another embodiment, two or more buttons 302 may be included, and different buttons may be configured to perform different functions. For example, the driving device 301 may be controlled to drive the ultrasonic transducer 203 to move in different directions. The button 302 may be positioned in a position that facilitates operation. For example, the button 302 may be positioned on the handle 205. The button 302 may also be positioned to be opposite the control unit 204, so that when the user holds the scanning assembly 200 with two hands, the control unit 204 may be operated with one hand, and the button 302 may be operated with the other hand, thereby enabling one operator to complete the operation. Moreover, in another embodiment, the above-described occasion may also be automatically implemented by the scanning assembly 200 (or an ultrasound imaging device). For example, when the scanning assembly 200 determines that the scanning assembly 200 is properly positioned and the compressive force for the scanning assembly is within a suitable range, the ultrasonic transducer 203 is automatically activated. A specific determination method is exemplarily described below.

Figure 4:
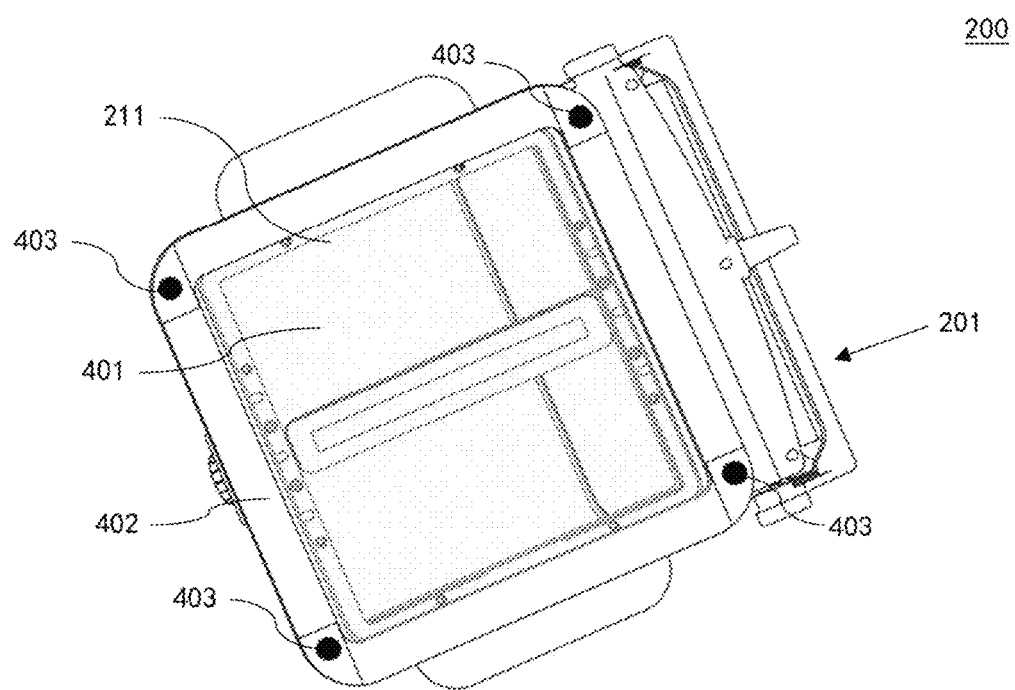
FIG. 4 shows a perspective view of a scanning assembly from the bottom according to some embodiments of the present application.

As described above in the present application, it is very important that the compressive force of the scanning assembly is controlled to be within a suitable range. In one aspect, the magnitude of the compressive force affects the image quality of ultrasound scanning, and in another aspect, the magnitude of the compressive force is also related to the safety of the person receiving a scan. In view of at least the above-described factors, improvements are provided in some embodiments of the present application. Referring to FIG. 4, FIG. 4 shows a perspective bottom view of the scanning assembly 200 according to some embodiments of the present application.

In some embodiments, the scanning assembly 200 further includes a film 401. The film 401 covers the opening 211. The compressive force can act on the tissue to be scanned (not shown in FIG. 4) by means of the film 401. As compared to directly pressing the housing 201 of the scanning assembly 200 onto the tissue to be scanned, the film 401 is provided to transmit the above-described compressive force, so that in one aspect, it is ensured that the compressive force is uniformly distributed, and in another aspect, the contact area of the tissue to be scanned can be increased, thereby improving safety. In one embodiment, the film 401 may be fixedly connected to the opening 211 on a lower portion of the scanning assembly 200. In another embodiment, the film 401 can be detachably connected to the scanning assembly 200. For example, an outer periphery of the film 401 may be fixed by means of the frame (not shown), and the film 401 may be detachably connected to the scanning assembly 200 by means of the frame. Alternatively, the film 401 may be directly detachably connected to the opening 211. The foregoing will not be further enumerated. In actual use, the film 401 may include media commonly used in ultrasound scanning, such as a coupling medium, etc., so as to facilitate the removal of air between the tissue to be scanned and the ultrasonic transducer. The film 401 may include a transparent material to facilitate the user to observe, from above through the film 401, the tissue to be scanned.

In some embodiments, the film 401 may at least include an air-impermeable flexible film layer. The flexible film can ensure that the film 401 is closely attached to the surface of the tissue to be scanned, thereby preventing air leakage. The air-impermeable flexible film can ensure that when a negative pressure is formed between the tissue to be scanned and the scanning assembly, the negative pressure directly acts on the air-impermeable flexible film, and the tissue to be scanned is tightly sucked by means of the air-impermeable flexible film. As compared to directly tightly sucking the tissue to be scanned, the air-impermeable film can further improve the degree of comfort and the scanning safety of the person receiving a scan. It can be understood that in some examples, the film 401 may include a plurality of layers of composite material. For example, the film 401 may include an air-permeable film and an air-impermeable film. The air-impermeable film is used to improve the degree of comfort of the person receiving a scan, and the air-permeable film is for penetration of the coupling medium.

To further improve the sealing between the scanning assembly 200 and the tissue to be scanned, the scanning assembly 200 in some embodiments of the present application further includes a seal ring 402. The seal ring 402 is made of a flexible material, and is disposed around the opening 211. The flexible material can ensure good contact between the seal ring 402 and the tissue to be scanned so as to prevent air leakage, and may specifically be of an arbitrary material type in the art, such as silicone, rubber, or the like. Details will not be described herein again. In addition, the seal ring 402 can further improve the degree of comfort of the person receiving a scan. In some examples, the seal ring 402 is configured to be connected around the opening 211. In some other examples, the seal ring 402 may also be configured to be integral with the film 401, so that when cleaning and sterilizing or replacement is needed, the seal ring 402 and the film 401 can be removed from the scanning assembly 200 simultaneously.

The scanning assembly 200 of the present application may further include a compressive force measurement unit. The compressive force measurement unit may be used to measure the compressive force of the scanning assembly 200 for the tissue to be scanned. Such a configuration means helps the compressive force borne by the tissue to be scanned to be accurately acquired in a scanning process, so that the scanning assembly 200 can control the pressure difference generating device of any embodiment described above to adjust the first pressure, thereby dynamically adjusting the compressive force.

In some embodiments, the compressive force measurement unit may include an air pressure sensor. The air pressure sensor is configured to be inside the housing 201 of the scanning assembly 200, so as to measure in real time the air pressure difference between the interior and the exterior of the housing 201. Further, the magnitude of the compressive force can be calculated according to the air pressure difference and the weight of the scanning assembly 200.

In some other embodiments, the compressive force measurement unit may, as shown in FIG. 4, include at least one force sensor 403. The force sensors 403 are disposed below the housing 201. The force sensors 403 can directly measure the compressive force acting on the surface of the tissue to be scanned. In one example, one force sensor 403 is provided. In another example, a plurality of force sensors 403 are provided and are uniformly distributed below the housing 201, a plurality of force sensors 403 enable more comprehensive and accurate measurements of the compressive force. Moreover, the difference between values of the plurality of force sensors 403 can further be used to determine whether the compressive force of the scanning assembly 200 on the tissue to be scanned is uniformly applied.

A method of using the scanning assembly disclosed in any embodiment described above is exemplarily described below.

In one example, the scanning assembly 200 described above can automatically regulate the compressive force. Specifically, the scanning assembly 200 may measure, in real time by means of the above-described compressive force measurement unit, the compressive force of the scanning assembly 200 acting on the tissue to be scanned. When a predetermined compressive force is reached, the pressure difference generating device can dynamically adjust the air pressure difference between the interior and the exterior of the scanning assembly 200 to adjust the first pressure, thereby achieving the objective of regulating the current compressive force. If the compressive force measurement unit detects that the current compressive force is smaller than the predetermined compressive force, the pressure difference generating device increases the air pressure difference to increase the compressive force. If the compressive force measurement unit detects that the current compressive force is greater than the predetermined compressive force, the pressure difference generating device automatically decreases the air pressure difference to decrease the compressive force. In this way, the compressive force is automatically maintained at a stable level, thereby facilitating ultrasound scanning. The predetermined compressive force may be configured by the user by operating the control unit as described above in the present application, or may be preset by the ultrasound imaging device.

In one example, the scanning assembly 200 described above may further be used to further ensure the safety of the person receiving a scan. For example, an upper limit of the compressive force may be preset. Once the compressive force measurement unit detects that the compressive force reaches the upper limit, the scanning assembly 200 may stop the pressure difference generating device operating, thereby rapidly decreasing the compressive force.

In one example, the scanning assembly 200 described above can further automatically scan the site to be scanned. For example, when the user correctly positions the scanning assembly 200 and activates the pressure difference generating device, the pressure difference generating device starts to gradually increase the air pressure difference to increase the compressive force. The process of increasing described above may be operated by the user, or may be automatically controlled by the pressure difference generating device. In this case, the compressive force measurement unit measures in real time the current compressive force. Once the compressive force reaches a predetermined value, in one aspect, the scanning assembly 200 may dynamically adjust the pressure difference generating device to cause the current compressive force to remain substantially stable, and in another aspect, the scanning assembly 200 may further automatically activate the ultrasonic transducer to perform scanning. In such an embodiment, the components cooperate with each other, thereby greatly enhancing the degree of automation and simplifying workflow.

It can be understood that the above merely exemplarily describes an operating means of the scanning assembly 200, and the actual operating means of the scanning assembly 200 may also be of other types. In addition, the scanning assembly 200 may further include other components, e.g., a processor circuit for cooperating with the component described in any embodiment described above to perform control. The processor circuit may be integrated in the scanning assembly 200, or may be integrated in the ultrasound imaging device connected to the scanning assembly 200. An ultrasound imaging device connected to the scanning assembly of any embodiment of the present application is exemplarily described below.

Figure 5:
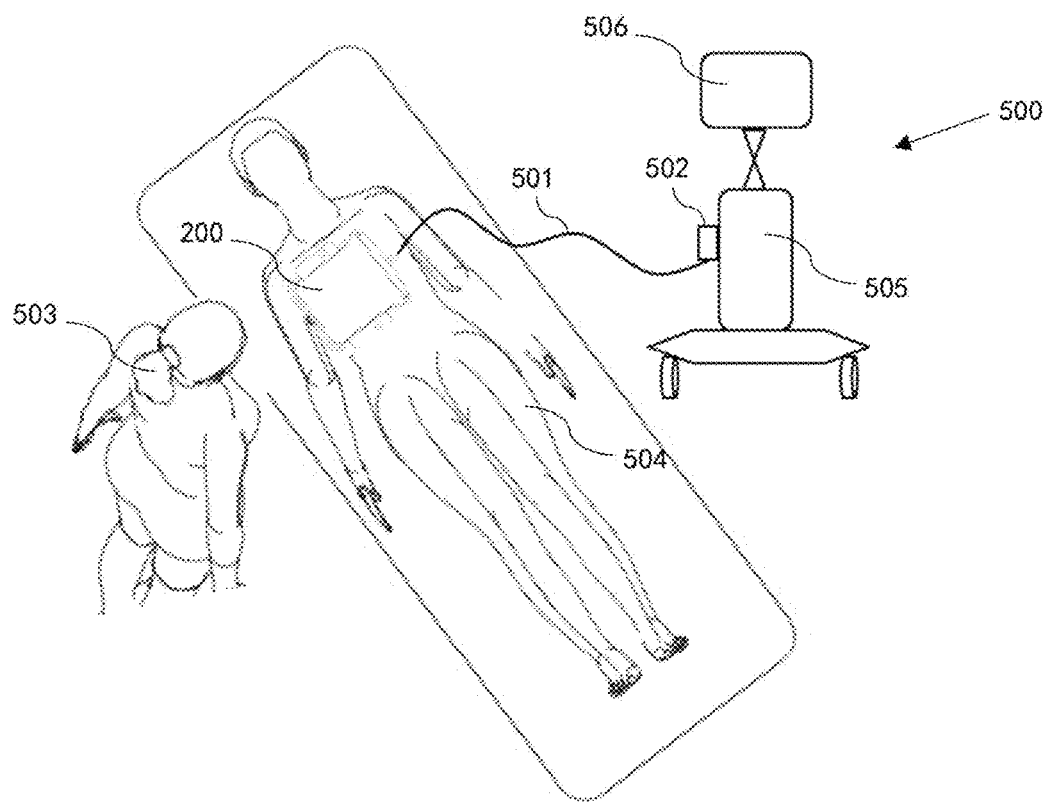
FIG. 5 shows a schematic diagram of an ultrasound imaging device comprising a scanning assembly according to some embodiments of the present application.

Referring to FIG. 5, FIG. 5 shows a schematic diagram of an ultrasound imaging device 500 including a scanning assembly according to some embodiments of the present application. The ultrasound imaging device 500 may include the scanning assembly described above in any described embodiment of the present application.

In the embodiments described in FIG. 5, the scanning assembly 200 may further include a cable 501 and a connector 502. One end of the cable 501 is connected to the scanning assembly 200. The connector 502 is connected to the other end of the cable 501. The scanning assembly 200 is electrically connected to the ultrasound imaging device 500 by means of the cable 501 and the connector 502, so that power and data transmission are performed by using the cable 501.

Such a configuration means ensures that the scanning assembly 200 is flexibly used. In particular, as compared to the existing ultrasound imaging device described above, the scanning assembly 200 no longer needs to be connected to the ultrasound imaging device by means of components including an adjustable arm, and is connected thereto by means of only the flexible cable. In addition, the pressure difference generating device described above is directly integrated on the scanning assembly 200, and likewise does not affect the flexibility of use of the scanning assembly 200. As shown in FIG. 5, an operator 503 can flexibly use the scanning assembly 200 to position a site to be scanned on a person 504 receiving a scan.

It should be noted that the connector 502 may be any type of connector in the prior art, and may be configured to be detachably connected to the ultrasound imaging device 500. For example, the ultrasound imaging device 500 may be a general-purpose ultrasound imaging device, and is adapted to be connected to different types of probes to scan different sites to be scanned. Such an ultrasound imaging device 500 typically has several probe connector sockets. Correspondingly, the connector 502 may be configured to match at least one socket. In which case, the scanning assembly 200 no longer needs to be configured with the dedicated ultrasound imaging device 500, and the scanning assembly 200 may be used as one of the ultrasound probes. Therefore, the versatility of the ultrasound imaging device 500 can be significantly improved. In another example, the connector may further be fixedly connected to the ultrasound imaging device 500, and details will not be described again.

The above-described scanning assembly 200 is an example of the present application. In another example, the cable and the connector may be removed. For example, the scanning assembly 200 may perform ultrasound scanning at a higher degree of freedom by means of modules such as an internal power source, the processor circuit, etc. The scanning assembly 200 may further have a built-in wireless signal receiving/sending module etc., to perform data transmission. In addition, the scanning assembly 200 may further be configured with a memory to store data and export the same by using a suitable means (e.g., to export the same in a wired or wireless means).

With continued reference to FIG. 5, other components of the ultrasound imaging device 500 are exemplarily described. In addition to the scanning assembly 200 of any embodiment described above, the ultrasound imaging device 500 may further include a main body 505 and a display 506.

The display 506 may be configured to display ultrasound image information acquired by means of ultrasound scanning, to allow the user to view the same. In another example, information related to parameters of scanning (such as the progress of scanning) may be sent to the display 506 so as to be displayed. The display 506 may include a user interface configured to display images or other information to the user. The type of the display 506 may be diverse, such as an LCD or OLED screen, or the like. In one example, the display 506 may further be configured to be a touch screen to facilitate the user in perform inputting.

The main body 505 may include a processor (not shown in the drawing). The processor (and a circuit thereof) may be used to control assemblies including the scanning assembly 200 so as to perform ultrasound scanning and process an echo signal to acquire an ultrasound image, and can control the display 506 to display the ultrasound image. In one example, the scanning assembly 200 described above in the present application performs an ultrasound scanning process independently. In another example, the above-described scanning process may be completed under the control of the processor in the main body 505. That is, when the scanning assembly 200 is electrically connected to the ultrasound imaging device 500, the processor can communicate with the scanning assembly 200, thereby sending/receiving data and controlling the scanning assembly 200. For example, the processor may be used to process data acquired by the ultrasonic transducer in the scanning assembly 200 by means of ultrasound scanning, so as to generate an ultrasound image. Further, the processor may further be configured to control the pressure difference generating device of the scanning assembly 200 on the basis of the ultrasound image, so as to adjust the first pressure. For example, as an alternative to the solution described in the above embodiments, the processor may determine quality of the ultrasound image by means of an algorithm, so as to automatically control the pressure difference generating device.

The main body 505 may further include a memory (not shown in the drawing). The memory may include movable and/or permanent apparatuses, and may include an optical memory, a semiconductor memory, and/or a magnetic memory, etc. The memory may include a volatile, non-volatile, dynamic, static, read/write, read only, random access, sequential access, and/or additional memory. The memory may store non-transitory instructions executable by the processor. The memory may further store raw image data received from the scanning assembly 200, a processed ultrasound image received from the processor, etc.

It can be understood that the above merely exemplarily describes the ultrasound imaging device 500. The ultrasound imaging device 500 may further be configured to include other parts, such as a user input device for facilitating human-machine interaction. The user input device may be the touch screen described above, or may be a mouse, a keyboard, or the like. The foregoing will not be further enumerated.

The purpose of providing the above specific embodiments is to allow the disclosure of the present application to be understood more thoroughly and comprehensively; however, the present application is not limited to said specific embodiments. A person skilled in the art should understand that various modifications, equivalent replacements, changes and the like can be further made to the present application and should be included in the scope of protection of the present application as long as these changes do not depart from the spirit of the present application.

The invention claimed is:

1. A scanning assembly, comprising:
  a housing, wherein a lower portion of the housing comprises an opening, and the opening being configured to be covered by tissue to be scanned;
  a pressure difference generating device disposed on the housing and used to generate an air pressure difference between the interior and the exterior of the housing, the air pressure difference providing a first pressure for the tissue to be scanned, the weight of the scanning assembly providing a second pressure for the tissue to be scanned, the tissue to be scanned being compressed under the action of a compressive force, and the compressive force comprising the first pressure and the second pressure; and an ultrasonic transducer disposed in the housing and used to perform ultrasound scanning on the compressed tissue to be scanned.

2. The scanning assembly according to claim 1, further comprising:
a film covering the opening, the compressive force acting on the tissue to be scanned by means of the film.

3. The scanning assembly according to claim 2, wherein the film at least comprises an air-impermeable flexible film layer.

4. The scanning assembly according to claim 1, further comprising:
a driving device connected to the ultrasonic transducer to drive the ultrasonic transducer to move.

5. The scanning assembly according to claim 4, wherein the driving device comprises an electric motor and a lead screw, the lead screw being horizontally disposed in the housing and being connected to the ultrasonic transducer, and the electric motor and the lead screw cooperating with each other to drive the ultrasonic transducer to move in the horizontal direction.

6. The scanning assembly according to claim 1, wherein the pressure difference generating device is configured to adjust the first pressure by adjusting the magnitude of the air pressure difference.

7. The scanning assembly according to claim 6, wherein the pressure difference generating device comprises a fan, and the rotational speed of the fan is configured to be adjustable to adjust the air pressure difference.

8. The scanning assembly according to claim 6, wherein the pressure difference generating device is further configured to automatically adjust the first pressure to keep the compressive force stable.

9. The scanning assembly according to claim 6, further comprising:
a control unit configured to, when operated, control the pressure difference generating device adjust the magnitude of the compressive force by adjusting the magnitude of the first pressure.

10. The scanning assembly according to claim 9, wherein the pressure difference generating device is further configured to, when the control unit is not operated, keep the compressive force stable by adjusting the magnitude of the first pressure.

11. The scanning assembly according to claim 9, further comprising:
a handle disposed on the housing, the control unit being disposed on the handle.

12. The scanning assembly according to claim 1, further comprising:
a compressive force measurement unit for measuring the compressive force.

13. The scanning assembly according to claim 12, wherein
the compressive force measurement unit comprises at least one force sensor, and the at least one force sensor is disposed below the housing.

14. The scanning assembly according to claim 1, further comprising:
a seal ring made of a flexible material and disposed around the opening.

15. The scanning assembly according to claim 1, further comprising:
a cable, one end of the cable being connected to the scanning assembly; and
a connector which is connected to the other end of the cable, the scanning assembly being electrically connected to an ultrasound imaging device by means of the cable and the connector, so that power and data transmission are performed by using the cable.

16. An ultrasound imaging device, comprising the scanning assembly according to claim 1.

17. The ultrasound imaging device according to claim 16, further comprising:
a processor configured to process data acquired by the ultrasonic transducer by means of ultrasound scanning to generate an ultrasound image, the processor being further configured to, on the basis of the ultrasound image, control the pressure difference generating device to adjust the first pressure.

* * * * *